United States Patent [19]

Forstrom et al.

[11] 4,230,663
[45] Oct. 28, 1980

[54] COLD GAS STERILIZATION PROCESS USING HYDROGEN PEROXIDE AT LOW CONCENTRATIONS

[75] Inventors: Richard J. Forstrom, Granada Hills; Michael D. Wardle, La Canada, both of Calif.

[73] Assignee: Moore-Perk Corporation, Indianapolis, Ind.

[21] Appl. No.: 56,177

[22] Filed: Jul. 10, 1979

Related U.S. Application Data

[62] Division of Ser. No. 836,665, Sep. 26, 1977, Pat. No. 4,169,124.

[51] Int. Cl.³ .................. A61L 2/20; A01N 59/00
[52] U.S. Cl. ........................... 422/33; 422/27; 422/28; 422/29; 424/130
[58] Field of Search ............. 422/28, 29, 30, 31, 422/32, 33, 34, 36, 37, 27; 424/130

[56] References Cited

U.S. PATENT DOCUMENTS

| | | | |
|---|---|---|---|
| 2,120,020 | 6/1938 | Coulter | 424/130 X |
| 2,193,622 | 3/1940 | Coulter | 424/130 |
| 2,368,806 | 2/1945 | Cook | 422/40 |
| 2,394,887 | 2/1946 | Berl | 422/122 X |
| 3,328,312 | 6/1967 | Laycock et al. | 422/4 |
| 3,854,874 | 12/1974 | Loliger et al. | 422/299 |
| 3,904,361 | 9/1975 | Egger | 422/27 |
| 3,912,451 | 10/1975 | Gaglea | 422/30 |
| 4,013,410 | 3/1977 | Thomas et al. | 422/30 |
| 4,169,123 | 9/1979 | Moore et al. | 422/29 |

*Primary Examiner*—Barry S. Richman
*Attorney, Agent, or Firm*—Larry N. Barger

[57] ABSTRACT

A "cold" gas sterilization process that operates at temperatures below 80° C. in a temperature range that is generally considered nonsporicidal. The process is capable of sterilizing with gaseous hydrogen peroxide at extremely low concentrations in a gas phase, such as 0.5 mg/L. The widely used process of "cold" sterilizing with ethylene oxide is typically run at a gas concentration of 630 mg/L and 55° C. Apparatus is also disclosed for use of this process in "cold" sterilization of contact lenses.

4 Claims, 2 Drawing Figures

COLD GAS STERILIZATION PROCESS USING HYDROGEN PEROXIDE AT LOW CONCENTRATIONS

This is a division of application Ser. No. 836,665 filed Sept. 26, 1977 and now U.S. Pat. No. 4,169,124 issued Sept. 25, 1979.

BACKGROUND OF THE INVENTION

U.S. Pat. Nos. 3,854,874 and 3,904,361 describe a process for sterilizing a web of packaging material by dip coating the web in a concentrated solution (10% to 40%) of hydrogen peroxide and then quickly evaporating the liquid film within 20 seconds as it travels through a hot chamber at temperatures of 80° C. to 120° C. where some hydrogen peroxide gas is generated for contact with the web.

Submersion of the web in concentrated liquid hydrogen peroxide solution would cause a "shock" effect on microorganisms making them easier to kill in the hot chamber. Also at 80° C. heat alone starts to become sporicidal and its sporicidal activity increases with temperature. It is noted that steam sterilization is carried out at 120° C. to 125° C. Although hydrogen peroxide gas is generated for contact with the packaging web, it is believed that sterilization occurs primarily because of the combined liquid and heat treatment.

Temperatures below 80° C. are generally considered nonsporicidal and a "cold" sterilizing process would operate in this range. The conventional ethylene oxide gas sterilization process is considered a "cold" process and typically operates at about 55° C.

The processes shown in the above two patents reduce viable bacterial spore population by only 5 log orders. The Food and Drug Administration (FDA) is currently recommending that all medical and surgical products be sterilized to a probability of survival for spores, which are the most resistant of cells to kill, of $10^{-6}$ or better. This means that the sporicidal activity of a sterilizing process must be so reliable as to assure the probability of less than 1 organism out of 1,000,000 will survive a sterilization cycle.

A "cold" sterilizing process that has produced survival probability sufficient for sterile medical and surgical products utilizing hydrogen peroxide gas has been described in a Moore and Perkinson patent application, Ser. No. 639,966, filed Dec, 11, 1975, and now abandoned. Such process operates at below 80° C. without requiring submersion in a concentrated hydrogen peroxide solution. Nothing is disclosed in such process relating to the space sterilized or the concentration of hydrogen peroxide in the gas phase. It is noted that the conventional ethylene oxide process is typically run at 55° C. with a gas phase concentration of 630 mg/L.

SUMMARY OF THE INVENTION

Our invention is an improvement on the basic "cold" sterilization process of Moore and Perkinson and involves the unexpected discovery that evaporation of large quantities of liquid hydrogen peroxide is not needed for sterilization. The present invention involved the discovery that extremely low concentrations of hydrogen peroxide in the gas phase, (such as 0.5 mg/L) can accomplish the same order of magnitude of sterilization as ethylene oxide at 630 mg/L in the gas phase as in current commercial use.

With this discovery, there is recognized a tremendous economic advantage over ethylene oxide gas sterilization as equivalent molecular amounts of hydrogen peroxide and ethylene oxide currently cost approximately the same. In addition, the low concentration of hydrogen peroxide gas is easy to dissipate from the sterilized product and does not require the extensive time necessary to eliminate ethylene oxide residues from the sterile product. A device for sterilizing contact lenses is shown using the "cold" hydrogen peroxide gas sterilization process. The device has structure for circulating hot tap water and for manual evacuation.

THE DRAWINGS

FIG. 1 is a side elevational view of a contact lens sterilization receptacle connected to an evacuating hypodermic syringe; and FIG. 2 is an enlarged view of the contact lens receptacle of FIG. 1 schematically showing a conduit for directing hot water through the receptacle.

DETAILED DESCRIPTION

Figure 1:
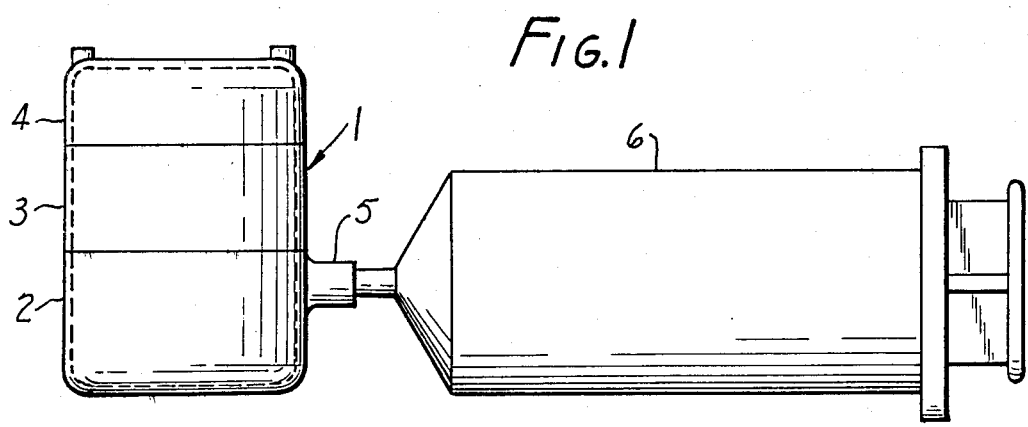

The following laboratory tests were run at the following hydrogen peroxide concentration in the gas phase.

EXAMPLE 1

Thirty silk sutures and 30 porcelain penicylinder carriers each inoculated with approximately $10^5$ mature spores of *Bacillus subtilis* var. *niger* were placed in a vessel under 25 in Hg negative pressure and an atmosphere of 1.1 mg $H_2O_2$/L was generated. After a 4 hour exposure at 55° C., testing of the carriers indicated them to be sterile.

EXAMPLE 2

Ten silk sutures and 10 procelain penicylinder carriers each inoculated with approximately $10^5$ mature spores of *Bacillus subtilis* var. *niger* were placed in a vessel under 25 in Hg negative pressure and an atmosphere of 0.6 mg $H_2O_2$/L was generated. After a 2 hour exposure at 60° C., testing of the carriers indicated them to be sterile.

EXAMPLE 3

Same procedure as in Example 2, except that 1.1 mg $H_2O_2$/L and 0.5 hours exposure at 55° were used. All carriers were rendered sterile.

EXAMPLE 4

Same procedure as in Example 1 with the substitution of approximately $10^2$ mature spores of *Clostridium sporogenes* per carrier. All carriers were rendered sterile.

EXAMPLE 5

Approximately $10^6$ mature spores of *Bacillus subtilis* var. *niger* on spore strips were placed in a vessel under 25 in Hg negative pressure and 1.4 mg $H_2O_2$/L was generated. After 1 hour exposure at 22° C., testing of the carriers indicated them to be sterile.

EXAMPLE 6

Same procedure as in Example 5 but without vacuum. After 24 hours exposure at 22° C., testing of the carriers indicated them to be sterile. Sterility was not achieved within 6 hours exposure.

While the variables of time, temperature, and $H_2O_2$ vapor concentration can be varied, the ranges of operation are 0.1 to 75 mg $H_2O_2$ vapor/L with a preferred range of 0.1 to 50 mg/L; 20°–80° C.; and 60 seconds to 24 hours time. In commercial use, the temperature might be in the range of 45°–65° C. and the time 10 minutes to 2 hours. The negative pressure applied is preferably greater than 15 inches of Hg.

The precise mechanism of why the hydrogen peroxide sterilizes at such extremely low concentrations is not fully understood. When a tiny amount of liquid hydrogen peroxide is introduced into a very large confined space, the water having a greater partial pressure in the vapor phase than the hydrogen peroxide evaporates quicker than the hydrogen peroxide. Thus, as the liquid phase becomes reduced in volume, it becomes more concentrated in hydrogen peroxide. As evaporation continues toward the end of the evaporative cycle, a greater hydrogen peroxide to water ratio is entering the gaseous phase. This might have an effect on the unexpected sporicidal activity of the low hydrogen peroxide gas concentration.

Experiments of Examples 5 and 6 relative to vacuum show that a vacuum can increase the killing rate severalfold. For instance, when 1.4 mg of $H_2O_2$ was added per liter of sterilizable space, the *Bacillus subtilis* spores were killed within 6–24 hours. When a vacuum of 24 inches of Hg was applied to a closed container, the time of kill decreased to 1 hour.

Throughout the specification hydrogen peroxide has been referred to relative to its concentration in its gaseous phase. Since this is a "cold" gas sterilization process similar to that of ethylene oxide, as opposed to a heat or liquid contact sterilization process, it is immaterial how the gaseous hydrogen peroxide concentration is obtained. A very small amount of liquid hydrogen peroxide could be placed inside of a package containing a product to be sterilized or inside of a sterilizer tank and then evaporated inside such package or tank to generate the desired concentration of hydrogen peroxide in gaseous phase. Alternatively, the vaporization process could be carried on outside of the package or sterilizing tank and gaseous hydrogen peroxide of the required concentration injected into the package or tank. If desired, a product to be sterilized could be packaged in a package that is pervious to hydrogen peroxide gas, but impervious to microbial passage.

It is recommended that a stabilized form of hydrogen peroxide be used. One such hydrogen peroxide that includes a stabilizer to prevent substantial catalytic decomposition caused by ions of aluminum, iron, copper, manganese, and chromium is marketed by F.M.C. Corporation of New York under the name Super D. Their technical bulletin No. 42 explains that a 6% solution retains 98% of its original active oxygen after being subjected to 100° C. for 24 hours. This is a more stringent temperature exposure than is utilized in the moderate temperatures of the present invention. A typical stabilizer for hydrogen peroxide might be sodium stannate as explained in the book entitled "Hydrogen Peroxide," by W. C. Schumb et al, Reinhold, 1955, pages 535–547.

An apparatus for sterilizing contact lenses using either the basic "cold" hydrogen peroxide sterilization process of Moore and Perkinson previously described, or the present improvement to that process is shown in the attached drawings. FIG. 1 schematically shows a receptacle 1 with a pair of joined compartments 2 and 3 respectively for holding each of a pair of contact lenses. The gas tight closure 4 on to the receptacle. This general construction of a contact lens receptacle that separates the two lenses to keep them from abrading against each other is conventional. What is not conventional is a vacuum port and adapter 5 that can connect to a piston type hypodermic syringe 6 for manually evacuating the contact lens receptacle.

Figure 2:
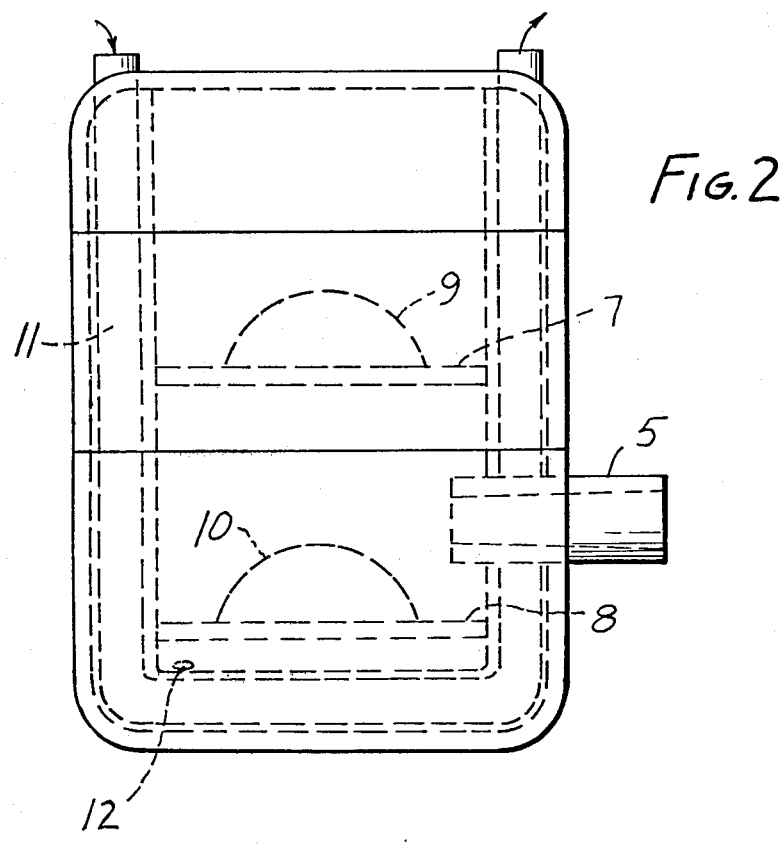

FIG. 2 is an enlarged view of the receptacle showing separate supporting surfaces 7 and 8 for the two contact lenses 9 and 10. Such lenses could be of the "soft" flexible plastic lenses that require frequent disinfection or sterilization to control growth of microorganisms on the lenses. Although not shown, it is understood that chambers containing lenses 9 and 10 are interconnected so hydrogen peroxide gas can freely circulate and contact both lenses.

In addition to evacuating the contact lens receptacle with syringe 6, it is preferred to elevate the receptacle's temperature in the range of 20° C. to less than 80° C., such as to 55° C. This can be done by circulating hot tap water through a conduit within the chamber shown schematically as 11. It is understood that other conduit structure could be used.

As shown in FIG. 2, the small droplet 12 of liquid hydrogen peroxide is in the receptacle. This droplet can be placed in the receptacle by the user and then evaporated to generate the necessary hydrogen peroxide gas. Alternatively, other means for generating the gas and introducing it into the receptacle could be used. After the lenses are sterilized, the receptacle is opened to vent the sterilizing gas and the lenses removed.

In the above described contact lens sterilization apparatus, the "cold" hydrogen peroxide gas sterilization process is preferably used to cause sporicidal kills of the magnitude recommended by the FDA for medical and surgical products, i.e. to a probability of survival of $1 \times 10^{-6}$ or better. The "cold" hydrogen peroxide gas sterilization process is very well suited for contact lenses because it is so convenient and fast. Depending on such factors as degree of vacuum applied, hydrogen peroxide gas concentration, and temperature, gas contact time can be in the range of 60 seconds to 1 hour. As shown in Example 3 above, a 1.1 mg/L concentration in the gas phase at 55° C. sterilizes in only 30 minutes. From calculations it is estimated that sterility occurs substantially sooner than this and there is a time safety factor in Example 3.

It is recognized that contact lenses are required to be sterile when sold. However, once in the hands of the user, the manufacturers of contact lenses are recommending periodic treatment by the user that merely disinfects the lenses. A liquid hydrogen peroxide solution is often recommended. A disinfectant is generally recognized as killing only vegetative cells, but not spores.

The reason manufacturers have not recommended full sterility of the magnitude recommended by the FDA for medical and surgical products, such as scalpels, sutures, hypodermic syringes, etc. is that there has been no convenient, economical and easily understandable device for use by the millions of people who now wear contact lenses. The present invention provides a simple economical device that a wearer can use to periodically sterilize rather than merely disinfect his contact lenses.

In the foregoing specification, specific examples have been used to describe this invention. However, those skilled in the art will understand how to make changes to these examples, without departing from the spirit and scope of the invention.

We claim:

1. A method of disinfecting a contact lens without substantial liquid contact which comprises: placing said lens in a sealed container; contacting the lens with hydrogen peroxide gas having a concentration of less than 75 mg/L; maintaining said gas in contact with such lens at temperatures below 80° C. until such lens has been disinfected; venting the gas from the container; and removing the lens from the container.

2. A method as set forth in claim 1, wherein the disinfecting method is also sporicidal rendering the lens sterile.

3. A method as set forth in claim 1, which further includes the step of evacuating the container after the lens has been placed in said container, and said gas is at less than atmospheric pressure for at least a portion of the time it is in contact with the lens.

4. A method as set forth in claim 1, wherein the disinfection is accomplished within the time range of 60 seconds to 1 hour.